United States Patent

Chazan et al.

[11] 3,959,255
[45] May 25, 1976

[54] ANTIBIOTIC AMINOGLYCOSIDES, AND PROCESS OF PREPARATION

[75] Inventors: Jean-Bernard Chazan, Paris; Daniel Coussediere, Villejuif; Jean-Claude Gasc, Bondy, all of France

[73] Assignee: Roussel-UCLAF, Paris, France

[22] Filed: Apr. 29, 1974

[21] Appl. No.: 464,934

[30] Foreign Application Priority Data

May 10, 1973  France .............................. 73.16882
Mar. 5, 1974  France .............................. 74.07410

[52] U.S. Cl. ..................... 260/210 AB; 260/210 K;
                                                        424/180
[51] Int. Cl.² ......................................... C07H 15/22
[58] Field of Search .................. 260/210 AB, 210 K

[56] References Cited
OTHER PUBLICATIONS
Journal of Antibiotics, vol. 21, No. 5, pp. 367–368, 1968.
Journal of Antibiotics, vol. 21, No. 5, pp. 365–366, 1968.

*Primary Examiner*—Johnnie R. Brown
*Attorney, Agent, or Firm*—Bacon & Thomas

[57] ABSTRACT

There are disclosed pharmaceutically-active aminoglycosides comprising 4-O-[2',6'-diamino-2',6'-didesoxy-α-D-glucopyranosyl] 6-O-[3''-methylamino-3'',4'',6''-tridesoxy-α-D-xylohexopyranosyl] 2-desoxy streptamine of the formula:

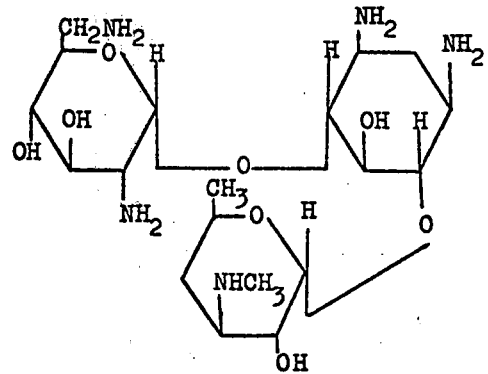

and the addition salts thereof with mineral acids or organic acids. Also disclosed are methods for preparation of the novel products as well as certain novel intermediate products. There are also disclosed pharmaceutical compositions in which the novel products are the active agents as well as methods for use of compositions as antibiotic agents.

5 Claims, No Drawings

ANTIBIOTIC AMINOGLYCOSIDES, AND PROCESS OF PREPARATION

The present invention concerns a new aminoglycoside compound and its salts. These compounds are pharmaceutically active as antibiotics. Thus, the main object of the present invention is a new derivative of the aminoglycoside family, namely the 4-O-[2',6'-diamino 2',6'-didesoxy α,D-glucopyranosyl] 6-O-[3''-methylamino 3'',4'',6''-tridesoxy α,D-xylohexopyranosyl] 2-desoxy streptamine of the following formula:

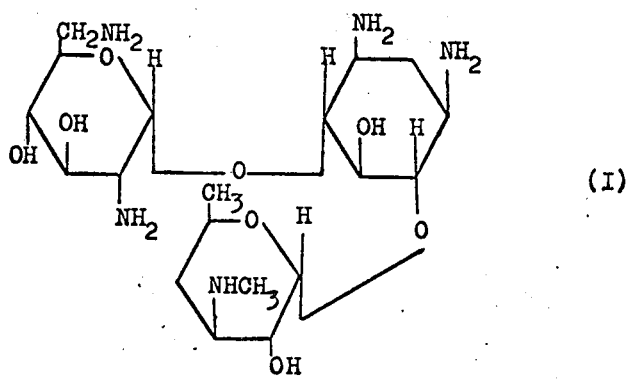

(I)

as well as its additive salts with mineral or organic acids. It is to be understood that addition salts may be formed with any mineral acid or organic acid providing the resulting product is non-toxic for the intended use. Methods for preparation of the various acid addition salts are well known in the art.

Among the salts of the product of formula I can be named, in particular, the sulfate of 4-O-[2',6'-diamino 2',6'-didesoxy α-D-glucopyranosyl] 6-O-[3''-methylamino 3'',4'',6''-tridesoxy α-D-xylohexopyranosyl] 2-desoxy streptamine, obtained by the action of sulfuric acid on the product of formula I in aqueous solution, and in which the five amino functions of the product of formula I are completely salified by sulfuric acid.

Other salts can also be obtained in which all of the amino functions of the product of formula I are salified or salts wherein the amino functions are only partially salified by the acid used to form the salts.

Other acids which can be used in forming salts include hydrochloric acid, phosphoric acid, hydrobromic acid, nitric acid, formic acid, citric acid, lactic acid, malic acid, maleic acid, succinic acid, tartaric acid, acetic acid, trifluoroacetic acid, benzoic acid, gluconic acid, ascorbic acid, sulfonic acid, para-toluenesulfonic acid, fumaric acid, methanesulfonic acid, and the like.

Another object of the invention is the provision of pharmaceutical compositions which include, as the active principle, the product of formula I or one of its therapeutically compatible salts.

The aforementioned products possess very interesting antibiotic activities both on the bacteria gram (+) such as Staphylococci, Streptococci and notably penicillin-resistant Staphylococci as well as on the bacteria gram (−), and notably coliform bacteria. Thus, they are useful in the treatment of humans and animals which are affected by these bacteria.

These properties render the product of formula I as well as its therapeutically compatible salts suitable for use as medication notably in the treatment of staphylococci such as those which are responsible for septicemia, skin diseases and infections on the face, pyodermites, septic or running sores, anthrax or carbuncles, phlegmons, erysipelas and the like. Also, acute staphylococci which arise in both the early and late stages of influenza, bronchopneumonia, and other infections of the lung including pulmonary suppuration can be treated by the products of this invention. Further, the products of the invention can be used against collibacilloses.

These products can be used parenterally, orally, rectally or locally by topical application on the skin or mucous membrane.

They can be given in the form of injectable solutions or suspensions, sterile powders for extemporaneous injectable preparations, tablets, capsules, syrups, suppositories, creames, pommades and aerosol preparations. These pharmaceutical forms are prepared according to the standard processes. The usual dose, varying according to the product used, the subject treated, and the affection concerned, can be from 100 mg. to 1 gram per day in a normal human being when administered parenterally.

The invention also comprises a process of preparation of the product of formula I above and of its salts, the process including a novel sequence of steps.

This process is characterized in that the product of formula:

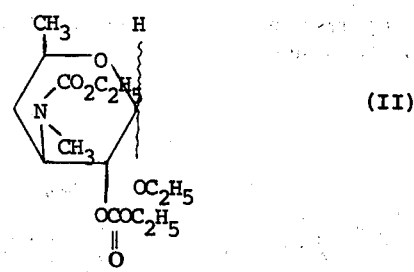

(II)

is made to react with an alkaline agent at room temperature to obtain the product of formula:

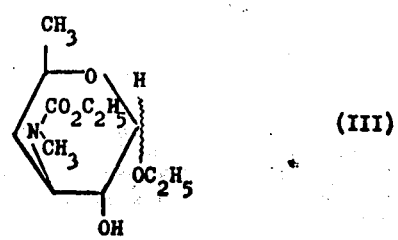

(III)

which is then treated with a benzyl halide in the presence of an alkaline agent to obtain the product of formula:

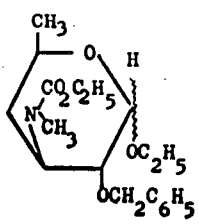
(IV)

which in turn is treated with acetic anhydride in acetic acid, in the presence of a strong acid to obtain the product of formula:

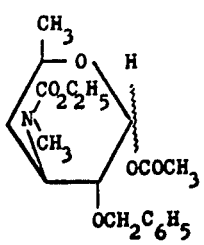
(V)

This product is then treated with anhydrous hydrochloric acid in the presence of acetyl chloride in an organic solvent medium to obtain the product of formula:

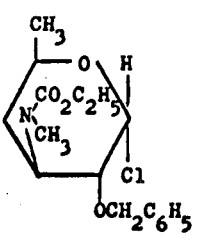
(VI)

The resulting product is then reacted with a product of the formula:

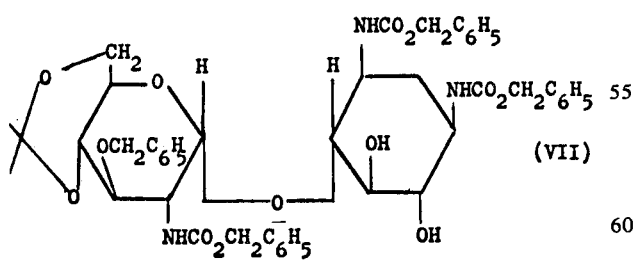
(VII)

in the presence of a catalyst to obtain the corresponding product in the form of a mixture of α and β anomers of the formula:

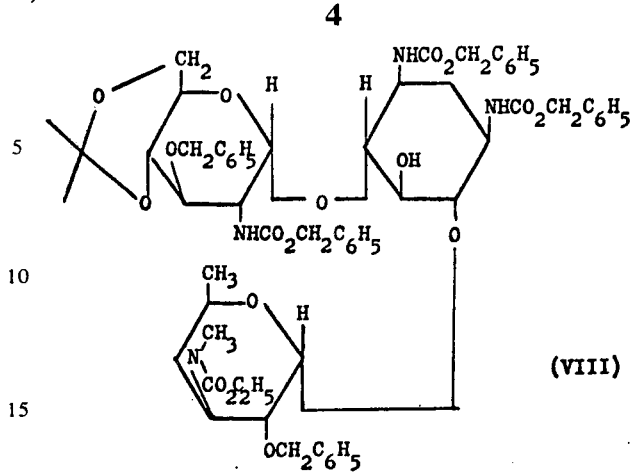
(VIII)

and:

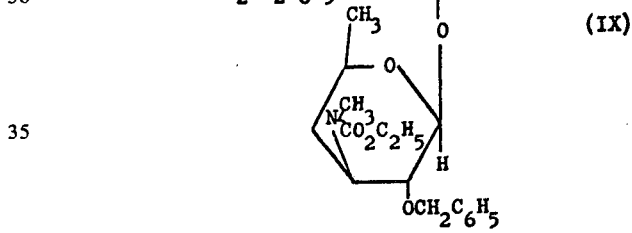
(IX)

From this mixture is separated the α anomer of formula VIII which is then treated by a dilute acid to obtain the product of the formula:

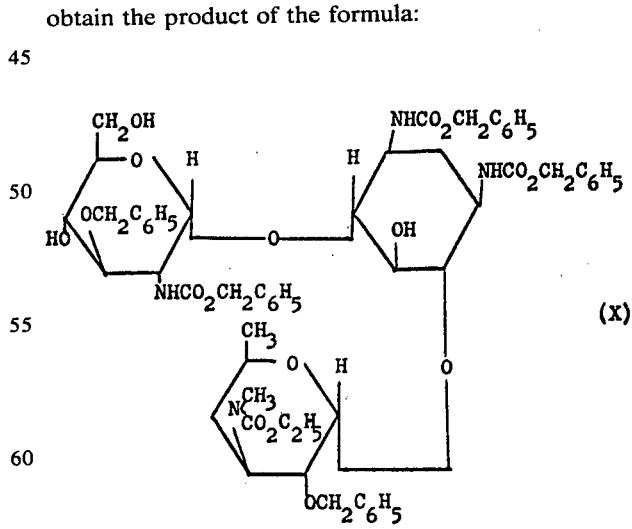
(X)

The latter product is then reacted with tosyl halide (chloride or bromide) in the presence of a base, preferably a tertiary amine, to form a product of the formula:

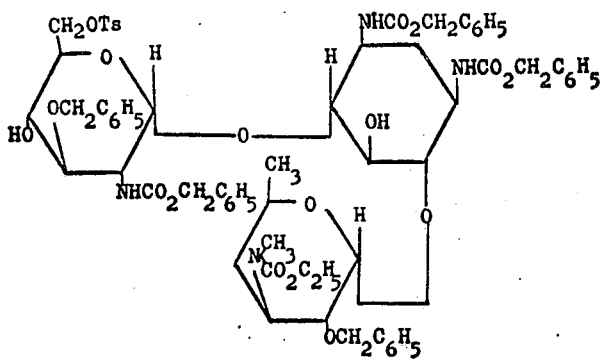

(XI) (where Ts=tosyl)

which in turn is treated with an alkali-metal nitride to form the corresponding azide of formula:

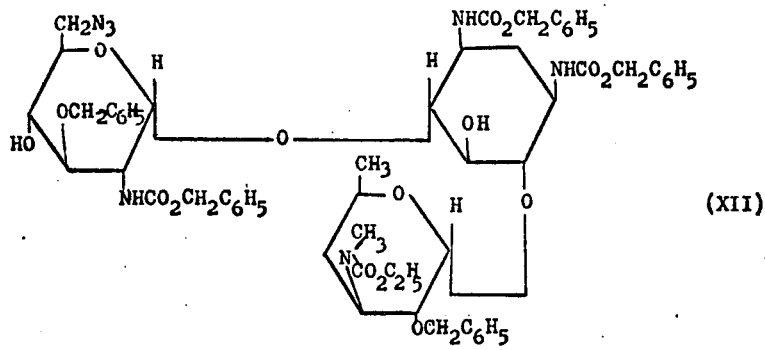

(XII)

The latter product is reduced by hydrogen in the presence of a catalyst and the methylamino function is liberated by treatment in alkaline medium to obtain the product of formula I. The salts of the formula I product can be obtained by the action of a mineral or organic acid thereon.

The preferred operating conditions in the broad process described above are as follows: The preferred alkaline agent which reacts on the product of formula II comprises an alkali metal hydroxide such as sodium hydroxide, or potassium hydroxide, an alkali metal carbonate or alkali metal bicarbonate such as $Na_2CO_3$, $K_2CO_3$, $NaHCO_3$, $KHCO_3$, etc. or baryta can also be used.

The preferred alkaline agent in whose presence the benzyl halide, which can be benzyl chloride or benzyl bromide, is made to react, is an alkali metal hydride, alkali metal amide or alkali metal hydroxide, preferably sodium hydride, sodium or potassium amide or sodium hydroxide. The alkaline agent is added at about room temperature, the mixture is then heated to reflux for a short time, cooled to room temperature and the benzyl halogenide added to complete the reaction. The resulting product of formula IV is then isolated and reacted with a strong acid in the presence of acetic anhydride to form the formula V product. The preferred strong acid is gasous hydrochloric acid, but one can also use other mineral acids, such as sulfuric acid; an organic acid such as trifluoracetic or p-toluene-sulfonic acid; a Lewis acid such as boron trifluoride or aluminum chloride or an ion-exchange resin of the sulfonic type. This reaction is conducted at room temperature.

The preferred organic solvent in which the reaction of the anhydrous strong acid with the formula V product in the production of the compound of formula VI occurs is dioxane; but ethyl ether, tetrahydrofuran or 1,2-dimethoxyethane can also be used.

The condensation reaction between the products of formulae VI and VII is a reaction of the type usually referred to as Koenigs-Knorr reaction and it is carried out in the presence of a catalyst which preferably comprises mercuric cyanide. However, one can also use other mercury salts, silver or cadmium salt, or a tertiary amine, such as collidine for example. The reaction is preferably carried out in an organic solvent medium and at the reflux point of the medium. Dioxane and benzene are especially preferred solvents. The separation of anomers of formula VIII or IX is realized by the usual physical methods; chromatography being preferred, but one can also use fractioned crystallization or countercurrent separation.

The preferred dilute acid used to transform the product of formula VIII into the product of formula X is an aqueous acetic acid, but one can also use other aqueous organic acids, such as for example, formic acid or trifluoracetic acid or an aqueous mineral acid such as hydrochloric acid or sulfuric acid. The reaction is preferably carried out at temperatures of about 45° to 70°C. The reaction with tosyl halide is carried out in pyridine solution.

As the hydrogenation catalyst to transform the product of formula XII, it is advantageous to use palladium deposited on coal black, but one can also use other palladium or platinum salts, derivatives of platinum and other catalysts, such as rhodium, ruthenium or nickel. The hydrogenation reaction is preferably carried out at a temperature of about 35° to 50°C.

The alkaline medium that is used to free the methylamino function of the product of formula XII is best composed of baryta dissolved in water, but other aqueous bases can be used such as sodium or potassium hydroxide for example.

The formation of salts of the product of formula I can be realized by the usual methods. They are preferably obtained by action on this product of a mineral acid such as hydrochloric acid or sulfuric acid, or an organic acid such as formic acid, benzoic acid or p-toluene-sulfonic acid. This salification is realized preferably in a solvent or mixture of solvents, such as water, ethyl ether, ethanol or acetone.

This process of the invention produces the new intermediate product of the formula:

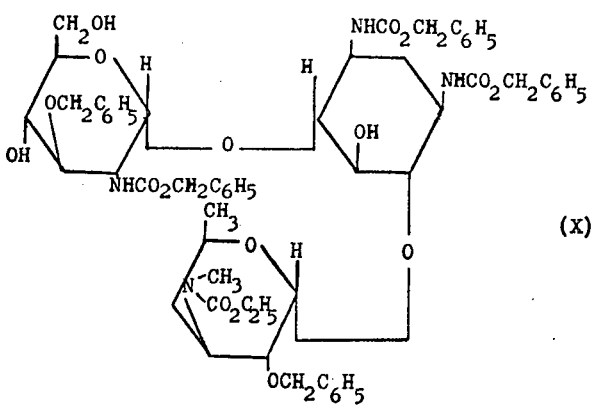

(X)

The following examples illustrate the invention without in anyway being limiting thereon.

EXAMPLE 1

4-O-[2',6'-diamino 2',6'-didesoxy α,D-glucopyranosyl]6-O-[3''-methylamino 3'',4'',6''-tridesoxy α,D-xylohexopyranosyl]2-desoxy streptamine.

Stage 1: Ethyl 3-(N-carbethoxy N-methyl) amino 3,4,6-tridesoxy D-xylohexopyranoside Sixty-seven grams of ethyl 3-(N-carbethoxy N-methyl) amino 3,4,6-tridesoxy 2-O-ethoxycarbonyl D-xylohexopyranoside (prepared according to J. Org. Chem., 1965, 30, 1287) are dissolved in 500 cm³ of ethanol, then 200 cm³ of 2N soda added thereto. The mixture is stirred for one hour at room temperature, then diluted with water and extracted with methylene chloride. The organic phase is rinsed with water and evaporated until dry in a vacuum to obtain 57 grams of the expected product in the form of a yellow oil which is used as is in the following stage.

Stage 2: Ethyl 2-O-benzyl 3-(N-carbethoxy N-methyl) amino 3,4,6-tridesoxy D-xylohexopyranoside Twelve grams of sodium hydride, dispersed in mineral oil, are placed in suspension in 300 cm³ of tetrahydrofuran. The solution of 57 g. of the product obtained in the preceding stage is added, under agitation, to 100 cm³ of tetrahydrofuran. It is heated to boiling and refluxed for 15 minutes, then cooled to 25°C. 29 cm³ of benzyl bromide are added and left for 15 hours at room temperature. The mixture is diluted with water and extracted with ethyl acetate. After evaporation of the ethyl acetate, the oil obtained is chromatographed on silica by means of a mixture of benzene-ethyl acetate (8:2). 60 G. of the expected product are obtained in the form of a white crystallized solid, m. pt. 65°C.

Stage 3: 1-O-acetyl 2-O-benzyl 3-(N-carbethoxy N-methyl) amino 3,4,6-tridesoxy D-xylohexopyranose Gaseous hydrochloric acid is bubbled into a mixture of 600 cm³ of acetic acid and 60 cm³ of acetic anhydride at 25°C. until saturation is completed. Then, 60 g. of the product obtained in the preceding stage are added and left for 16 hours at room temperature while continuing bubbling of the hydrochloric acid into the mixture. The mixture is then evaporated until dry in a vacuum not exceeding 40°C.

The oil obtained is chromatographed on silica by means of a mixture of chloroform acetone (9:1). As a result 60 g. of the expected product are obtained in the form of a white crystallized solid.

The α anomer has been obtained in pure form by recrystallization from isopropyl ether.

Analysis: ($C_{19}H_{27}NO_6$): Calculated: C%62.45; H%7.45; N%3.83; Found: C%62.7; H%7.7; N%3.7

Stage 4: 4-O-[2'-(N-carbobenzoxy) amino 2'-desoxy 3'-O-benzyl 4',6'-O-isopropylidene α,D-glucopyranosyl]6-O-[2''-O-benzyl 3''-(N-carbethoxy N-methyl) amino 3'',4'',6''-tridesoxy D-xylohexopyranosyl]1,3-dibenzyloxycarbonyl 2-desoxy streptamine anomers α and β

Sixty grams of the product obtained from the preceding stage are dissolved in one liter of dioxane containing 4.5% of gaseous hydrochloric acid and 500 cm³ of acetyl chloride. It is brought to 37°C. over one hour then evaporated in a vacuum. The residue obtained is dissolved in 100 cm³ of dioxane and the resultant solution is poured into a refluxing solution of 40 g. 4-O-[2'-(N-carbobenzoxy) amino 2'-desoxy 3'-O-benzyl 4',6'-O-isopropylidene α,D-glucopyranosyl]1,3-dibenzyloxycarbonyl 2-desoxy streptamine, (prepared according to Bull. Chem. Soc. Japan, 1969, 42, 529) in 200 cm³ of dry dioxane and 400 cm³ of benzene containing 40 g. of anhydrous calcium sulfate and 50 g. of mercuric cyanide. The heating is continued at reflux for 2½ hours, then cooled. The reaction mixture is filtered and the filtrate is treated with an aqueous solution of sodium bicarbonate. It is extracted with ethyl acetate and the organic phase is evaporated until dry in a vacuum. The residue is chromatographed three times on silica by means of a benzene-ethyl acetate mixture (7:3), and 22.9 g. of the α anomer of the expected product and 7.2 g. of the β anomer are obtained.

Anomer α : $α_D^{20} = +59°$ (c = 0.5%, chloroform)

Rf = 0.43 (Silica; benzene-ethyl acetate 1:1).

Anomer β : $α_D^{20} = +18°$ (c + 0.5%, chloroform)

Rf = 0.3 (Silica; benzene-ethyl acetate 1:1).

Stage 5: 4-O-[2'-(N-carbobenzoxy) amino 2'-desoxy 3'-O-benzyl 6'-O-tosyl α,D-glucopyranosyl]6-O-tosyl 2''-O-benzyl 3''-(N-carbethoxy N-methyl) amino 3'',4'',6''-tridesoxy α,D-xylohexopyranosyl] 1,3-dibenzyloxycarbonyl 2-desoxy streptamine 5.5 Grams of the α-anomer obtained in the preceding stage are dissolved in 30 cm³ of acetic acid containing 6 cm³ of water.

The solution is heated to 60°C. for one hour, then recooled and the water is added. The formed precipitate is dried, washed with water and drained. It is then dissolved in 12 cm³ of pyridine and 2.1 g. of tosyl chloride are added to the solution.

The reactants are left in contact for two hours at room temperature; then ice and hydrochloric acid are added until a pH of 2 is reached. The mixture is extracted with methylene chloride and the organic phase is rinsed with water. It is evaporated in a vacuum and 4.6 g. of the expected product are obtained in the form of a white solid which is used as such in the following stage.

Rf = 0.48 (Silica; chloroform-acetone 8:2)
Analysis: ($C_{67}H_{78}N_4O_{19}S$): Calculated: S% 2.5; Found: S% 2.3

Stage 6: 4-O-[2'-(N-carbobenzoxy) amino 6'-azido 3'-O-benzyl 2',6'-didesoxy α,D-glucopyranosyl] 6-O-[2''-O-benzyl 3''-(N-carbethoxy N-methyl) amino 3'',4'',6''-tridesoxy α,D-xylohexopyranosyl] 1,3-dibenzyloxycarbonyl 2-desoxy streptamine 4.6 Grams of the product obtained in the preceding stage are dissolved in 20 cm³ of dimethylformamide, 1.6 g. of sodium nitride are added and the mixture is heated to 100°C. for four hours. After recooling, water is added and the precipitate obtained is dried. Four grams of the expected product are obtained in the form of a white solid.

Analysis: ($C_{60}H_{71}N_7O_{16}$): Calculated: N% 8.55; Found: N% 8.5

Rf = 0.24 (Silica; chloroform-acetone 9:1)

Stage 7: 4-O-[2',6'-diamino 2',6'-didesoxy α,D-glucopyranosyl] 6-O-[3''-methylamino 3'',4'',6''-tridesoxy α,D-xylohexopyranosyl]2-desoxy streptamine Four grams of the product obtained in the preceding stage are dissolved in 160 cm³ of ethanol containing 2 cm³ of concentrated hydrochloric acid. Four grams of palladium deposited on coal black at a 10% concentration are added and agitated in a hydrogen atmosphere at 40°C. 12 Grams of catalyst and 100 cm of water are re-added 3 times. At the end of 3 hours, the mixture is recooled, the catalyst is filtered off and the filtrate is alkalized by means of an ion exchange resin in basic form. The resin is separated and the solution is dried in a vacuum.

A white solid is obtained which is dissolved in 50 cm³ of water to which is added 15 g. of baryta. The mixture is heated to 90°C. for 16 hours, recooled and brought to pH = 3 with a sulfuric acid N solution. The filtrate is filtered and alkalized by means of an ion exchange resin of the quaternary ammonium type in basic form. The resin is separated and evaporated to dryness in a vacuum.

An amorphous product is obtained which is purified by passage through a column of ion exchange resin of the carboxylic acid type in the ammonium form by means of 0.1 and 0.2N ammonia elution. The resultant product is then chromatographed on silica by means of a mixture of chloroform-methanol-ammonia (2:2:1).

Thus, 0.93 g. of the expected product are obtained in the amorphous form. This is the final product of Example 1.

$[\alpha]_D^{20} = 137.5°$ (c = 0.5%, water).

Analysis: ($C_{19}H_{39}N_5O_8$ + ½ $C_2H_5OH$ + 5 $H_2O$); Calculated: C% 41.51; H% 9.06; N% 12.10; Found: C% 41.2; H% 8.7; N% 12.2

Rf = 0.48 (Cellulose; Chloroform-Methanol-Ammonia 2:2:1).

EXAMPLE 2

Sulfate of 4-O-[2',6'-diamino 2',6'-didesoxy α,D-glucopyranosyl] 6-O-[3''-methylamino 3'',4'',6''-tridesoxy α,D-xylohexopyranosyl] 2-desoxy streptamine Two grams of 4-O-[2',6-diamino 2',6'-didesoxy α,D-glucopyrannosyl] 6-O-[3''-methylamino 3'',4'',6''-tridesoxy α,D-xylohexopyrannosyl] 2-desoxy streptamine are dissolved in 20 cm² of water. The resultant solution is agitated and there are added 18.6 cm³ of normal sulfuric acid. The pH of the resultant solution is 4.5. To this solution are added 100 mg. of active carbon, followed by agitation for 15 minutes and then filtration. The cold filtrate is concentrated in a vacuum until reaching a 5 cm³ volume, and 80 cm³ of methanol are added. The resultant precipitate is then dried, rinsed in methanol and dried.

As a result there are recovered 3 grams of the sulfate of 4-O-[2',6'-diamino 2',6'-didesoxy α,D-glucopyrannosyl] 6-O-[3''-methylamino 3'',4'',6''-tridesoxy α,D-xylohexopyrannosyl] 2-desoxy streptamine in the form of a white solid of formula:

$C_{19}H_{39}N_5O_8$, 5/2 $SO_4H_2$ $[\alpha]_D^{20} = +95°$ (c = 0.5%, in water)

EXAMPLE 3

An injection preparation is prepared as follows:

| | |
|---|---|
| Final Product of Example 1 | 50 mg. |
| Sterile Aqueous Excipient | 1 cm³ |

EXAMPLE 4

An injection preparation is prepared as follows:

| | |
|---|---|
| Sulfate Product of Example 2 | 100 mg. |
| Sterile Aqueous Excipient | 1 cm³ |

PHARMACOLOGICAL STUDY a. In vitro antibacterial activity

The antibacterial activity has been measured in vitro by the method of dilution in liquid, using Kanamycin as a comparison.

A series of tubes is prepared in which is distributed the same quantity of nutritive medium. Increasing quantities of the antibiotic under study are distributed, then each tube is inoculated with a bacterial stock. After a 24, 48 or 72 hours incubation in a 37° oven, inhibition of the bacterial growth is appraised by transillumination which determines the minimal inhibiting concentrations (CMI) of the products, expressed here as µg/cm³. The product described in Example 1 will be called product A and the product described in Example 2 will be called product B in the following tables:

| STOCKS | Product A CMI in µg/cm³ | | Product B CMI in µg/cm³ Per Free Base | | | Kanamycin CMI in µg/cm³ | |
|---|---|---|---|---|---|---|---|
| | 24h. | 48h. | 24h. | 48h. | 72h. | 24h. | 48h. |
| Staphylococcus Oxford U.C. 1061 Penicillino-sensible | 0.2 | 0.2 | 0.5 | 0.5 | 0.5 | 2 | 2 |
| Staphylococcus aureus UC 1128 Penicillino-resistant | 0.4 | 1 | 0.2 | 0.5 | 0.5 | 3 | 5 |
| Streptococcus Hemolyticus 905 | >40 | | 40 | 100 | 100 | >40 | |
| Streptococcus faecalis 5432 | >40 | | >100 | | | >40 | |
| Bacillus Subtilis | ≤0.05 | ≤0.05 | ≤0.05 | ≤0.05 | ≤0.05 | 0.1 | 0.6 |

| STOCKS | Product A CMI in µg/cm³ | | Product B CMI in µg/cm³ Per Free Base | | | Kanamycin CMI in µg/cm³ | |
|---|---|---|---|---|---|---|---|
| | 24h. | 48h. | 24h. | 48h. | 72h. | 24h. | 48h. |
| Escherichia Coli UC. 1020 | 0.6 | 1 | | 1 | 1 | 5 | 5 |
| Pseudomonas Pyocyanea | >40 | | >100 | | | >40 | |
| Enterobacter Aerogenes 6086 | 0.4 | 0.6 | | | | 3 | 3 |
| Klebsiella Pneumonia 52145 | 0.1 | 0.1 | 0.2 | 0.2 | 0.2 | 0.4 | 0.4 |
| Salmonella Typhimurium 420 | 5 | 20 | | | | 2 | 5 |
| Proteus Mirabilis A 235 | 1 | 2 | 2 | 2 | 2 | 2 | 5 |
| Proteus Morgani A 236 | 0.2 | 0.6 | | | | 0.4 | 0.4 |
| Shigella Sonnei | 3 | 10 | | | | 0.6 | 1 |
| Escherichia Coli UC 1261 | | | 0.5 | 0.5 | 1 | | |
| Escherichia Coli Taylor | | | 0.5 | 0.5 | 0.5 | | | b. In vivo antibacterial activity

The antibacterial activity has been measured in vivo on an experimental Escherichia Coli infection on mice, using gentamycin as a comparison.

Seventy mice with a medium weight of 30 g. are arranged in 7 series of 10 mice. An intraperitoneal infection with 0.5 cm³ of an Escherichia Coli (Taylor $O_{26}B_{26}$) culture in Pasteur nutritive bouillon diluted to 1/4.5 with distilled water is conducted. Treatment is performed by subcutaneous administration of product A or gentamycin 3 times - 1 hour, 5 hours and 23 hours after the infection. The mortality rate 22 hours and 3 days after the infection and the number of surviving mice after 8 days are noted.

The results are summarized in the following table:

| DOSAGE | Mortality at 22 hours | 3 days | Survived to the eighth day |
|---|---|---|---|
| Distilled Water | | | |
| 3 × 0.5 cm³ | 10 | — | 0 |
| Product A | | | |
| 3 × 0.015 mg | 7 | 9 | 1 |
| 3 × 0.030 mg | 0 | 1 | 9 |
| 3 × 0.50 mg | 0 | 0 | 10 |
| Gentamycin | | | |
| 3 × 0.015 mg | 3 | 7 | 3 |
| 3 × 0.030 mg | 0 | 0 | 10 |
| 3 × 0.050 mg | 0 | 0 | 10 |

The invention has been described herein with reference to certain preferred embodiments. However as obvious variations thereon will become apparent to those skilled in the art, the invention is not to be limited thereto.

What is claimed is:
1. The 4-O-[2',6'-diamino 2',6'-didesoxy α,D-glucopyranosyl] 6-O-[3''-methylamino 3'',4'',6''-tridesoxy α,D-xylohexopyranosyl] 2-desoxy streptamine of the formula:

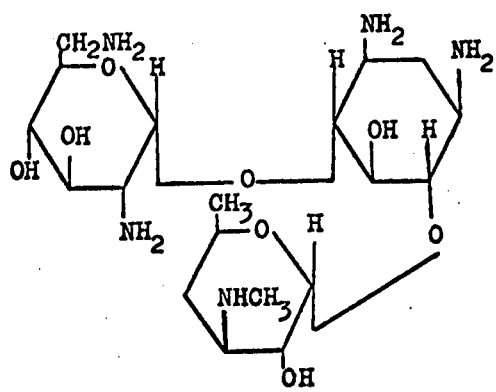

and its pharmaceutically acceptable salts.

2. A product according to claim 1 which is the sulfate of 4-O-[2',6'-diamino 2',6'-didesoxy α,D-glucopyranosyl] 6-O-[3''-methylamino 3'',4'',6''-tridesoxy α,D-xylohexopyranosyl] 2-desoxy streptamine.

3. A process for the preparation of the product of claim 1 which consists essentially of reacting a compound of the formula:

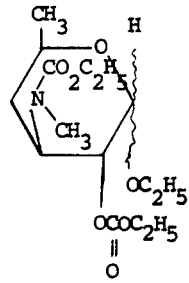

with an alkaline agent selected from the group consisting of alkali metal hydroxide, alkali metal carbonate, alkali metal bicarbonate and baryta at room temperature to obtain the compound of the formula:

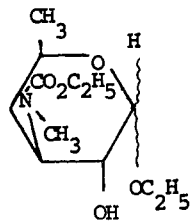

treating the latter product with a benzyl halide in the presence of an alkaline agent selected from the group consisting of alkali metal hydride, alkali metal amide and alkali metal hydroxide to obtain a compound of the formula:

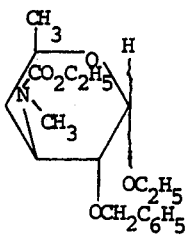

treating the latter product with acetic anhydride in acetic aicd in the presence of a strong acid selected from the group consisting of mineral acids, organic acids, Lewis acids and an ion-exchange resin of the sulfonic type to obtain the product of the formula:

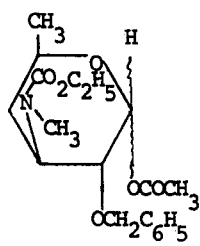

treating the latter product with an anhydrous hydrochloric acid in the presence of acetyl chloride in an organic solvent selected from the group consisting of dioxane, ethyl ether, tetrahydrofuran and 1,2 dimethoxyethane to obtain the product of the formula:

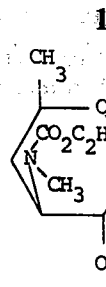

reacting the latter product with a compound of the formula:

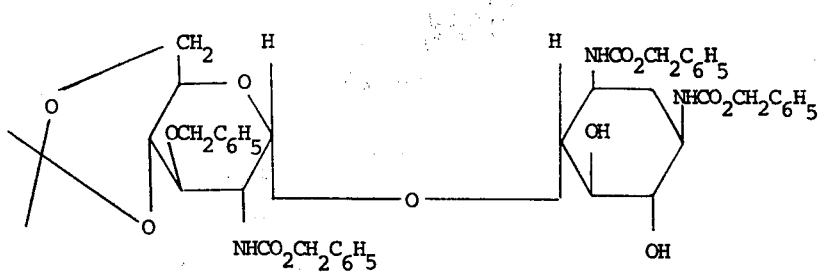

in the presence of a catalyst selected from the group consisting of mercury salts and tertiary amine to obtain the correcponding product in the form of a mixture of the α-anomer of the formula:

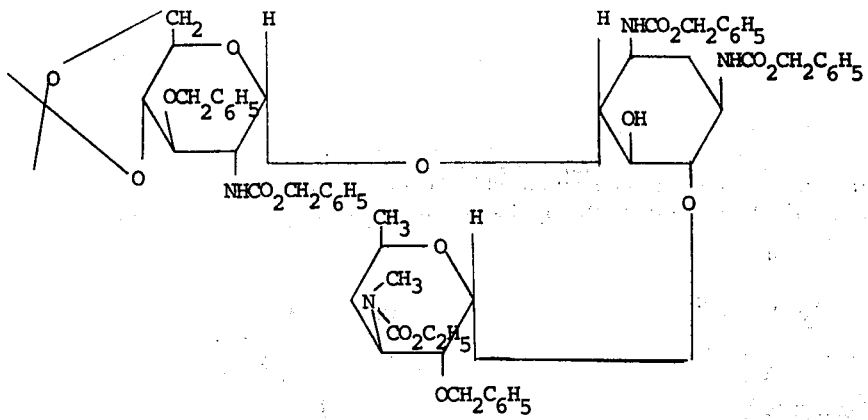

and the β-anomer of the formula:

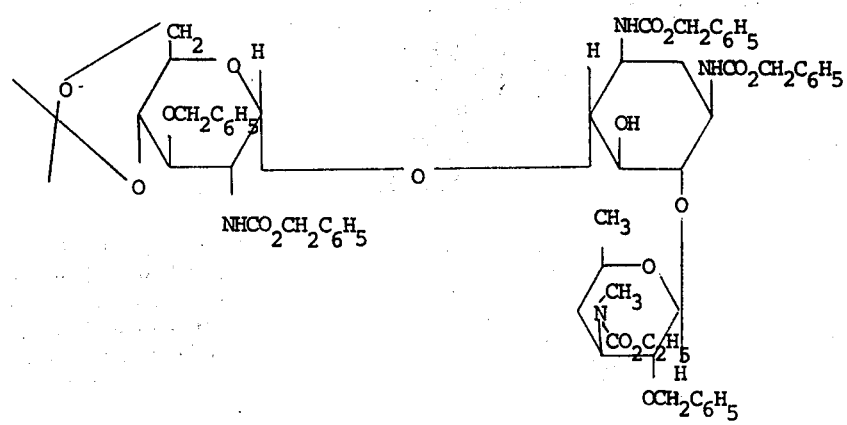

separating the α- and β-anomers, treating the α-anomer with a dilute acid selected from the group consisting of an aqueous organic acid and an aqueous mineral acid to obtain the product of the formula:

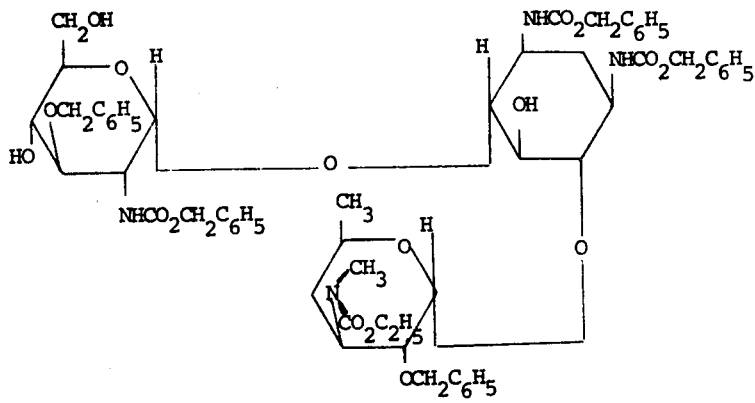

where Ts is tosyl, reacting the latter product with alkali metal nitride to obtain the azide of the formula:

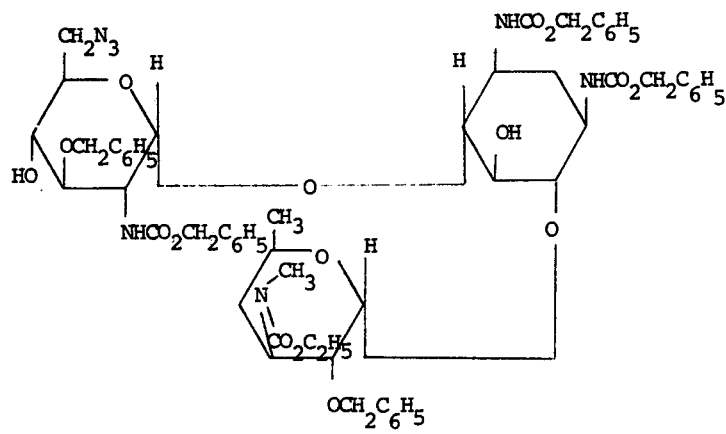

treating the latter product with tosyl halide in the presence of a base to obtain the product of the formula:

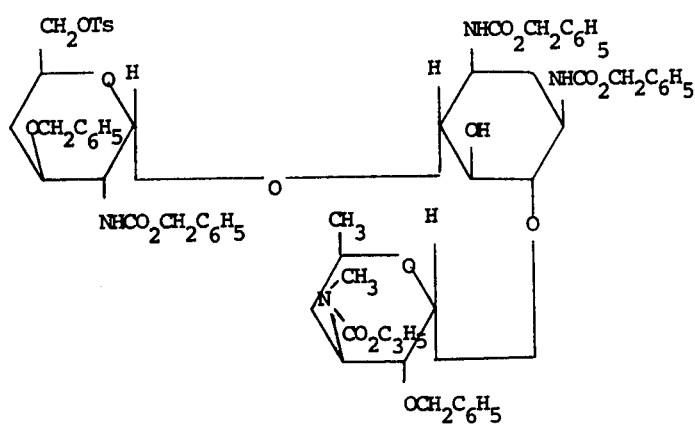

reducing the latter compound in the presence of hydrogen and a hydrogenation catalyst, treating the resulting compound with an alkaline medium to free the methylamino function and obtain the product of claim 1.

4. The compound of the formula:

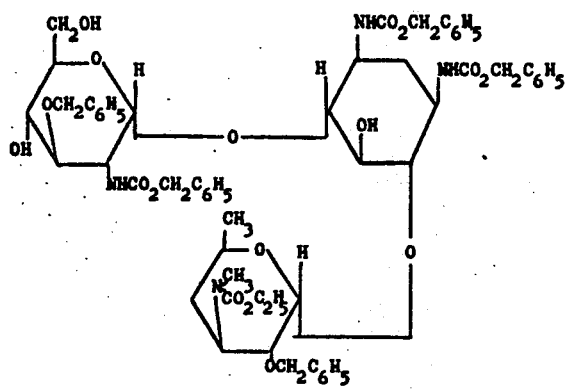

5. A product according to claim 1 wherein the pharmaceutically acceptable salt is obtained with sulfuric acid, hydrochloric acid, phosphoric acid, hydrobromic acid, nitric acid, formic acid, citric acid, lactic acid, malic acid, maleic acid, succinic acid, tartaric acid, acetic acid, trifluoroacetic acid, benzoic acid, gluconic acid, ascrobic acid, sulfonic acid, para-toluenesulfonic acid, fumaric acid, or methanesulfonic acid.

* * * * *